US011723569B2

(12) United States Patent
Wang et al.

(10) Patent No.: US 11,723,569 B2
(45) Date of Patent: Aug. 15, 2023

(54) METHODS OF IDENTIFYING SCHIZOPHRENIA PATIENTS AT RISK FOR RELAPSE

(71) Applicant: JANSSEN PHARMACEUTICA NV, Beerse (BE)

(72) Inventors: Dai Wang, Bridgewater, NJ (US); Srihari Gopal, Belle Mead, NJ (US); Vaibhav Narayan, Princeton, NJ (US); Adam Savitz, Greenwich, CT (US); Susan Baker, Pennington, NJ (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 1579 days.

(21) Appl. No.: 15/818,903

(22) Filed: Nov. 21, 2017

(65) Prior Publication Data
US 2018/0140242 A1 May 24, 2018

Related U.S. Application Data

(60) Provisional application No. 62/434,587, filed on Dec. 15, 2016, provisional application No. 62/425,257, filed on Nov. 22, 2016.

(51) Int. Cl.
*A61B 5/16* (2006.01)
*G01N 33/74* (2006.01)
*A61K 31/519* (2006.01)
*A61B 5/145* (2006.01)
*G01N 33/68* (2006.01)
*A61P 25/18* (2006.01)
*A61B 5/00* (2006.01)

(52) U.S. Cl.
CPC .............. *A61B 5/167* (2013.01); *A61B 5/165* (2013.01); *A61K 31/519* (2013.01); *A61P 25/18* (2018.01); *G01N 33/6869* (2013.01); *G01N 33/6893* (2013.01); *G01N 33/743* (2013.01); *A61B 5/14546* (2013.01); *A61B 5/4088* (2013.01); *A61B 5/4839* (2013.01); *A61B 5/7275* (2013.01); *G01N 2333/5412* (2013.01); *G01N 2333/7155* (2013.01); *G01N 2800/302* (2013.01); *G01N 2800/50* (2013.01); *G01N 2800/54* (2013.01)

(58) Field of Classification Search
CPC ....... A61B 5/165; A61B 5/4839; A61B 5/167; A61P 25/18; G01N 2800/302; G01N 33/743; G01N 2800/50
See application file for complete search history.

(56) References Cited

U.S. PATENT DOCUMENTS

| | | | |
|---|---|---|---|
| 7,838,246 | B2 | 11/2010 | Bahn |
| 7,981,684 | B2 | 7/2011 | Levin et al. |
| 9,861,307 | B2 | 1/2018 | Klin et al. |
| 2007/0172831 | A1 | 7/2007 | Altar et al. |
| 2012/0208718 | A1 | 8/2012 | Gault et al. |
| 2014/0350000 | A1 | 11/2014 | Brennan et al. |
| 2016/0003849 | A1 | 1/2016 | Arnoldussen et al. |
| 2017/0016921 | A1 | 1/2017 | Bahn et al. |

FOREIGN PATENT DOCUMENTS

| | | |
|---|---|---|
| EP | 3037996 A2 | 6/2016 |
| JP | 2011-506995 A | 3/2011 |
| WO | 03/066039 | 8/2003 |
| WO | 2009/077763 A1 | 6/2009 |
| WO | 2011/142460 A1 | 11/2011 |

OTHER PUBLICATIONS

Van Meijel et al., Int. J. Mental Health, 2004, 13: 107-16.*
Leucht et al., "Relapse prevention in schizophrenia with new-generation antipsychotics: a systematic review and exploratory meta-analysis of randomized, controlled trials", Am J Psychiatry, vol. 160, No. 7, Jul. 2003, pp. 1209-1222.
Cordon et al., "Descriptive analyses of the aripiprazole arm in the risperidone long-acting injectable versus quetiapine relapse prevention trial (ConstaTRE)", Eur Arch Psychiatry Clin Neurosci, vol. 262, No. 2, Mar. 2012, pp. 139-149.
Ainsworth, et al., A Comparison of Two Delivery Modalities of a Mobile Phone-Based Assessment for Serious Mental Illness: Native Smartphone Application vs Text-Messaging Only Implementations, Journal Of Medical Internet Research, Apr. 5, 2013, pp. 1-21, vol. 15 Issue 4.
Ben-Zeev, et al., Predictors of Self-Stigma in Schizophrenia: New Insights Using Mobile Technclogies, Journal of Dual Diagnosis, 2012, pp. 305-314, vol. 8 Issue 4.
Berwaerts, et al., Efficacy and Safety of the 3-Month Formulation of Paliperidone Palmitate vs Placebo for Relapse Prevention of Schizophrenia: A Randomized Clinical Trial, JAMA Psychiatry, Mar. 29, 2015, pp. E1-E10, vol. 72.
Birchwood, et al., Predicting relapse in schizophrenia: the development and implementation of an early signs monitoring system using patients and families as observers, a preliminary investigation, Psychological Medicine, 1989, pp. 649-656, vol. 19.
Emsley, et al., . The nature of relapse in schizophrenia, BioMed Central Psychiatry, 2013, pp. 1-8, vol. 13 Issue 50.
Faurholt-Jepsen, et al., Smartphone data as objective measures of bipolar disorder symptoms, Psychiatry Research, Mar. 13, 2014, pp. 124-127, vol. 217.
Gaebel, et al., Early neuroleptic intervention to schizophrenia: are prodromal symptoms valid predictors of relapse?. British Journal of Psychiatry, 1993, pp. 8-21, vol. 163 Supplementary 21.

(Continued)

*Primary Examiner* — Olga N Chernyshev
(74) *Attorney, Agent, or Firm* — Wan Chieh Lee; Haug Partners LLP

(57) ABSTRACT

The invention provides methods of identifying schizophrenia patients at risk for relapse. The invention also provides methods of early detection of schizophrenic relapse. The disclosed methods use monitoring of a subset of symptoms and/or one or more biomarkers. The symptom severity can be assessed using the Positive and Negative Syndrome Scale (PANSS) parameters. The methods of the invention can be used to provide early intervention to decrease or prevent relapse in schizophrenia patients.

20 Claims, 10 Drawing Sheets

(56) References Cited

OTHER PUBLICATIONS

Gaebel, et al., Revisiting the relapse predictive validity of prodromal symptoms in schizophrenia, Schizophrenia Research, Jul. 13, 2007, pp. 19-29, vol. 95.
Gleeson, et al., Early warning signs of relapse following a first episide of psychosis, Schizophrenia Research, Aug. 24, 2005, pp. 107-111, vol. 80.
Gumley, et al., Early intervention for relapse in schizophrenia: results of a 12-month randomized controlled trial of cognitive behavioural therapy, Psychological Medicine, 2003, pp. 419-431, vol. 33.
Heinrichs, et al., Prospective Study of Prodromal Symptoms in Schizophrenic Relapse, Am. J. Psychiatry, 1985, pp. 371-373, vol. 142 Issue 3.
Herz, et al., Relapse in schizophrenia, Am. J. Psychiatry, 1980, pp. 801-805, vol. 137 Issue 7.
Hirsch, et al., The Dysphoric Syndrome in Schizophrenia and its Implications for Relapse, British Journal of Psychiatry, 1989, pp. 46-50, vol. 155 Supplementary 5.
Hough, et al., Paliperidone palmitate maintenance treatment in delaying the time-to-relapse in patients with schizophrenia: A randomized, double-blind placebo-controlled study, Schizophrenia Research, Dec. 2, 2009, pp. 107-117, vol. 116.
Kay, et al., The positive and negative syndrome scale (PANSS) for schizophrenia, Schizophrenia Bulletin, 1987, pp. 261-276, vol. 13 Issue 2.
Komatsu, et al., Effectiveness of Information Technology Aided Relapse Prevention Programme in Schizophrenia excluding the effect of user adherence: A randomized controlled trial, Schizophrenia Research, Aug. 31, 2013, pp. 240-244, vol. 150.
Malla, et al., Prodromal symptoms in schizophrenia, British Journal of Psychiatry, 1994, pp. 487-493, vol. 164.
Marder, et al., Early prediction of relapse in schizophrenia: an application of receiver operating characteristic (ROC) methods, Psychopharmacology Bulletin, 1991, pp. 79-82, vol. 27 Issue 1.
Meijel, et al., Recognition of early warning signs in patients with schizophrenia: A review of the literature, International Journal of Mental Health Nursing, 2004, pp. 107-116, vol. 13.
Morriss, et al., Training to Recognise the Early Signs of Recurrence in Schizophrenia, Schizophrenia Bulletin, Jan. 15, 2013, pp. 255-256, vol. 39 Issue 2.
Palmier-Claus, et al., The feasibility and validity of ambulatory self-report of psychotic symptoms using a smartphone software application, BioMed Central Psychiatry, 2012, pp. 1-10, vol. 12 Issue 172.
Per Jorgensen., Early signs of psychotic relapse in schizophrenia, British Journal of Psychiatry, 1998, pp. 327-330, vol. 172.
Spaniel, et al., ITAREPS: Information Technology Aided Relapse Prevention Programme in Schizophrenia, Schizophrenia Research, Oct. 24, 2007, pp. 312-317, vol. 98.
Spaniel, et al., The Information Technology Aided Relapse Prevention Programme in Schizophrenia: an extension of a mirror-design follow-up, Int J Clin Pract, 2008, pp. 1943-1946, vol. 62.
Subotnik, et al., . Prodromal Signs and Symptoms of Schizophrenic Relapse, Journal of Abnormal Psychology, 1988, pp. 405-412, vol. 97 Issue 4.
Tait, et al., The development and implementation of an individualised early signs monitoring system in the prediction of relapse in schizophrenia, Journal of Mental Health, Jul. 6, 2009, pp. 141-153, vol. 11 Issue 2.
Tarrier, et al., Prodromal signs of relapse in schizophrenia, Social Psychiatry and Psychiatric Epidemiology, 1991, pp. 157-161, vol. 26.
Wang, et al., CrossCheck: Towards passive sensing and detection of mental health changes in people with schizophrenia, Proc. Int. Conf. Ubiquitous Comput, Sep. 12, 2016, pp. 1-12, page number.
Kramer, M. et al. Paliperidone extended-release tablets for prevention of symptom recurrence in patients with schizophrenia: a randomized, double-blind, placebo-controlled study. J. Clin. Psychopharmacol. 27, 6-14 (2007).
Savitz, et al., Efficacy and Safety of Paliperidone Palmitate 3-month Formulation for Patients with Schizophrenia: A randomized, Multicenter, Double-blind, Noninferiority Study, International Journal of Neuropsychopharmacology, (2016) 19(7): 1-14.
PCT ISR PCT/US2017/62682, dated May 15, 2018.
Birchwood, et al., Schizophrenia: early warning signs, Advances in Psychiatric Treatment, 2000, pp. 93-101, vol. 6 Issue 2.
Borovcanin, et al., Elevated serum level of type-2 cytokine and low IL-17 in first episode psychosis and schizophrenia in relapse, Journal of Psychiatric Research, Aug. 14, 2012, pp. 1421-1426, vol. 46 Issue 11.
Borovcanin, et al., Increase systemic levels of IL-23 as a possible constitutive marker in schizophrenia, Psychoneuroendocrinology, Mar. 3, 2015, pp. 143-147, vol. 56.
CHEN_ET_AL_2005, A prospective 3-year longitudinal study of cognitive predictors of relapse in first-episode schizophrenic patients, Schizophrenia Research, Apr. 6, 2005, pp. 99-104, vol. 77 Issue 1.
Hayashi-Takagi, et al., Peripheral Biomarkers Revisited: Integrative Profiling of Peripheral Samples for Psychiatric Research, Biol Psychiatry, 2014, pp. 920-928, vol. 75 Issue 12.
Lipkovich, et al., Predictors of risk for relapse in patients with schizophrenia or schizoaffective disorder during olanzapine drug therapy, Journal of Psychiatric Research, 2007, pp. 305-310, vol. 41.
Miller, et al., Meta-Analysis of Cytokine Alterations in Schizophrenia: Clinical Status and Antipsychotic Effects, Biol Psychiatry, Apr. 1, 2011, pp. 663-671, vol. 70 Issue 7.
Muller, et al., Soluble IL-6 receptors in the serum and cerebrospinal fluid of paranoid schizophrenic patients, Eur Psychiatry, 1997, pp. 294-299, vol. 12 Issue 6.
Schennach, et al., Predictors of Relapse in the Year After Hospital Discharge Among Patients With Schizophrenia, Psychiatric Services, 2012, pp. 87-90, vol. 63 Issue 1.
Schwarz, et al., Identification of a biological signature for schizophrenia in serum, Molecular Psychiatry, 2012, pp. 494-502, vol. 17.
Schwarz, et al., Identification of blood-based molecular signatures for prediction of response and relapse in schizophrenia patients, Transl Psychiatry, Jan. 8, 2012, pp. 1-9, vol. 2 Issue 82.
Van Kammen, et al., Elevated interleukin-6 in schizophrenia, Psychiatry Research, May 31, 1999, pp. 129-136, vol. 87.
Wunderink, et al., Predictive Validity of Proposed Remission Criteria in First-Episode Schizophrenic Patients Responding to Antipsychotics, Schizophrenia Bulletin, Aug. 7, 2006, pp. 792-796, vol. 33 Issue 3.
Boyer L, et al., Quality of life is predictive of relapse in schizophrenia. BMC Psychiatry. 13:15, pp. 1-8 (Jan. 9, 2013).
Mondelli V, et al., Cortisol and Inflammatory Biomarkers Predict Poor Treatment Response in First Episode Psychosis. Schizophrenia Bulletin. vol. 41, No. 5, pp. 1162~1170 (Mar. 31, 2015).
Office Action issued in the corresponding Korean patent application No. 10-2019-7017879 dated Jan. 11, 2023.

* cited by examiner

FIGS. 1A-1D
FIG. 1A
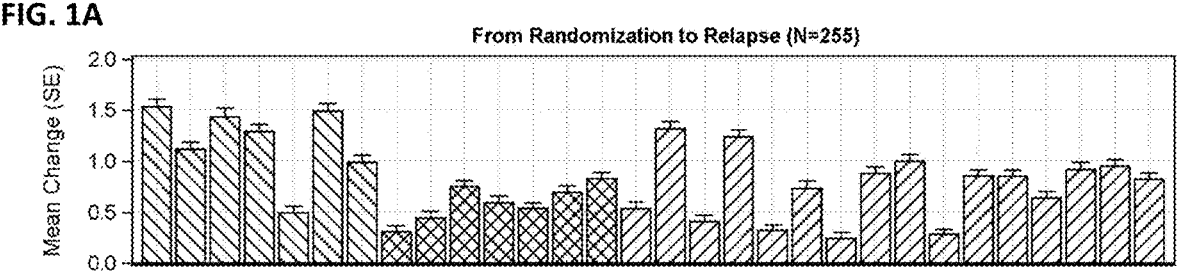
FIG. 1B
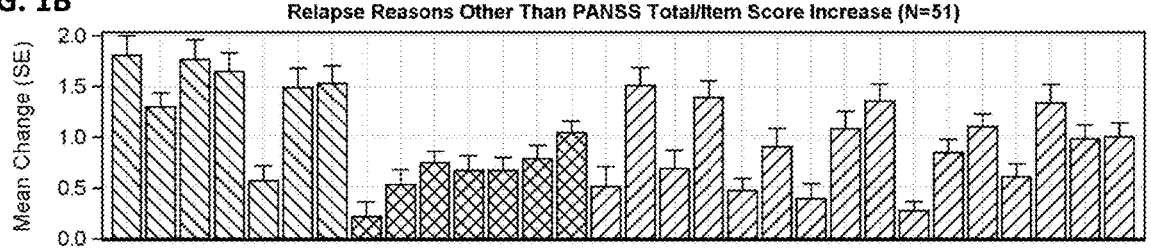
FIG. 1C
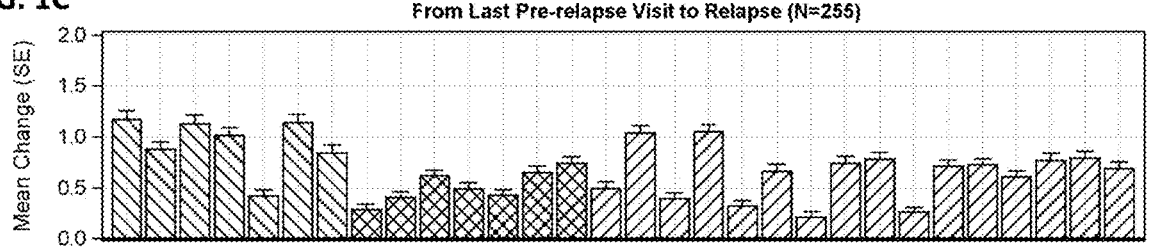
FIG. 1D
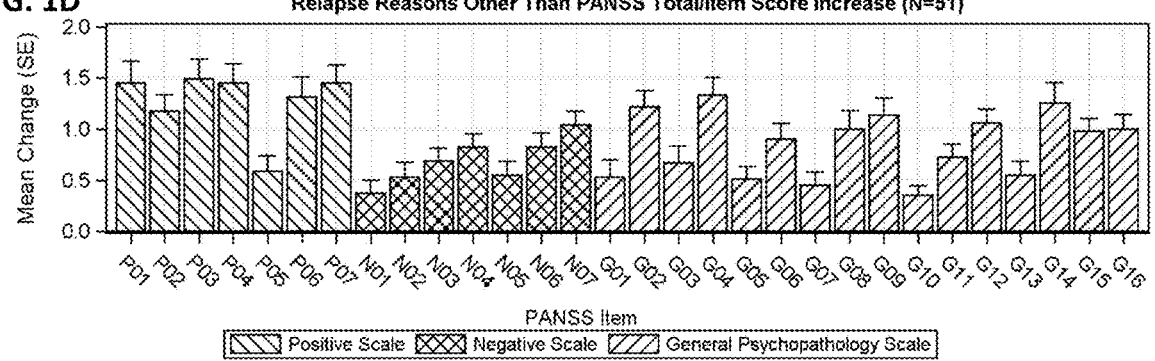

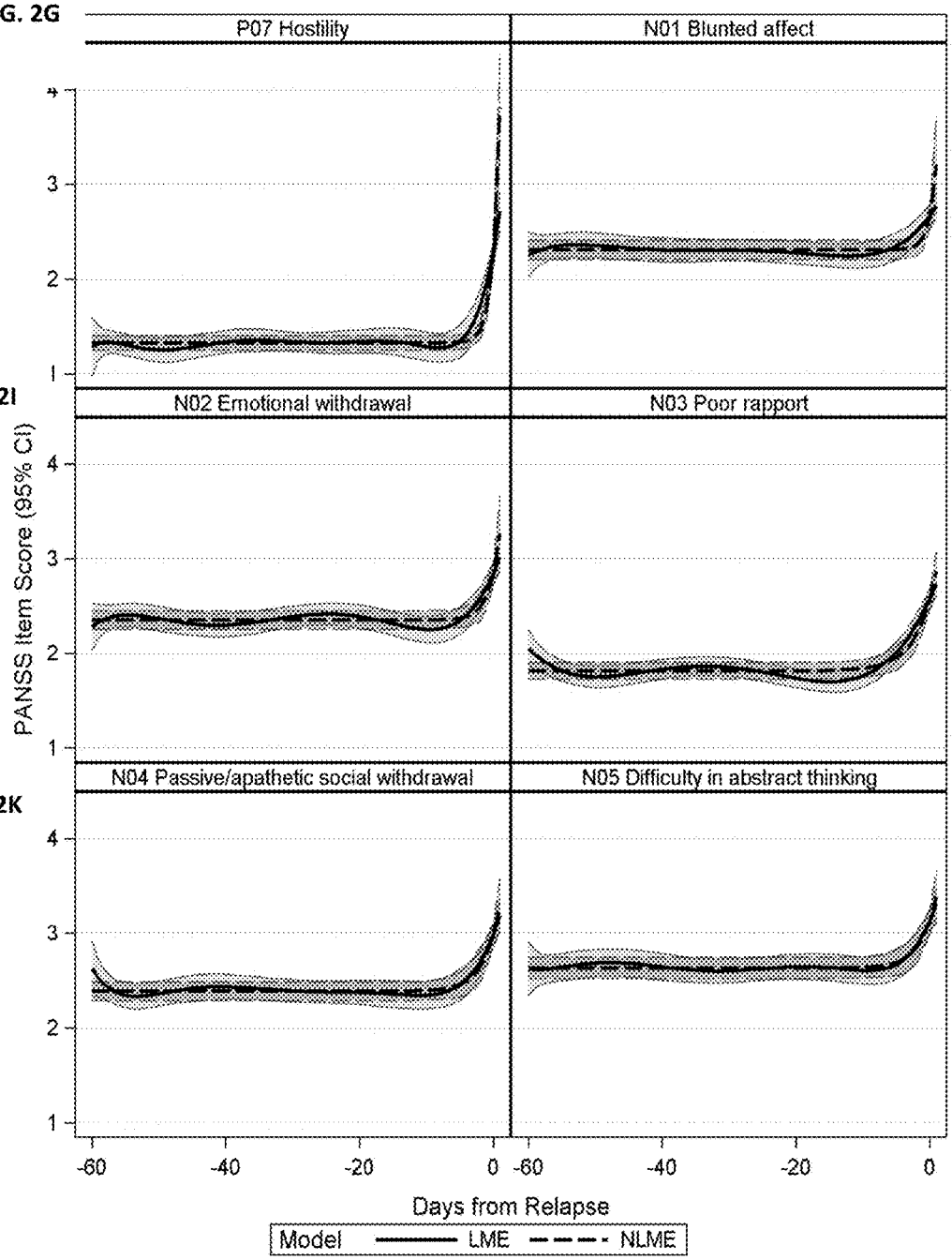

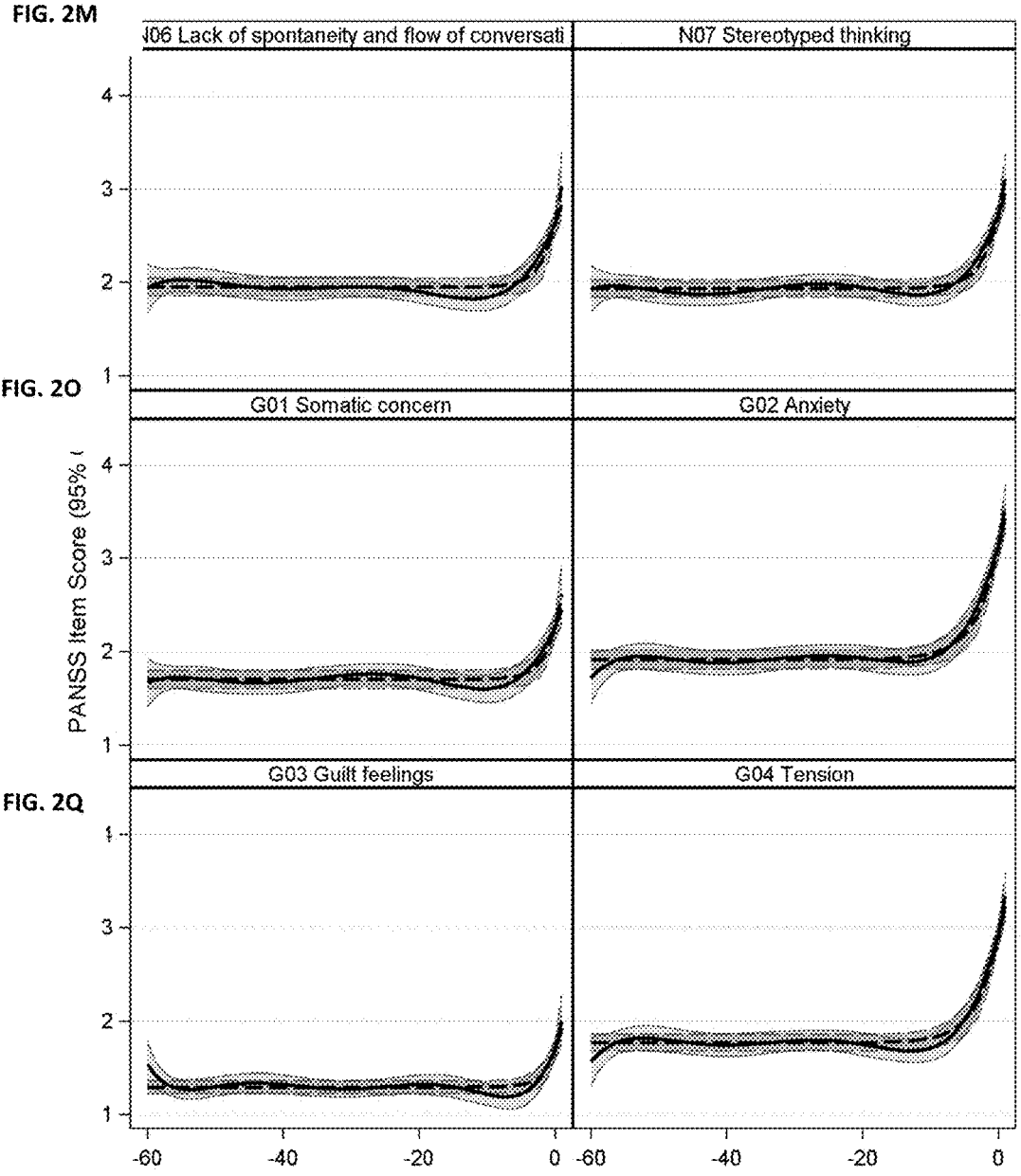

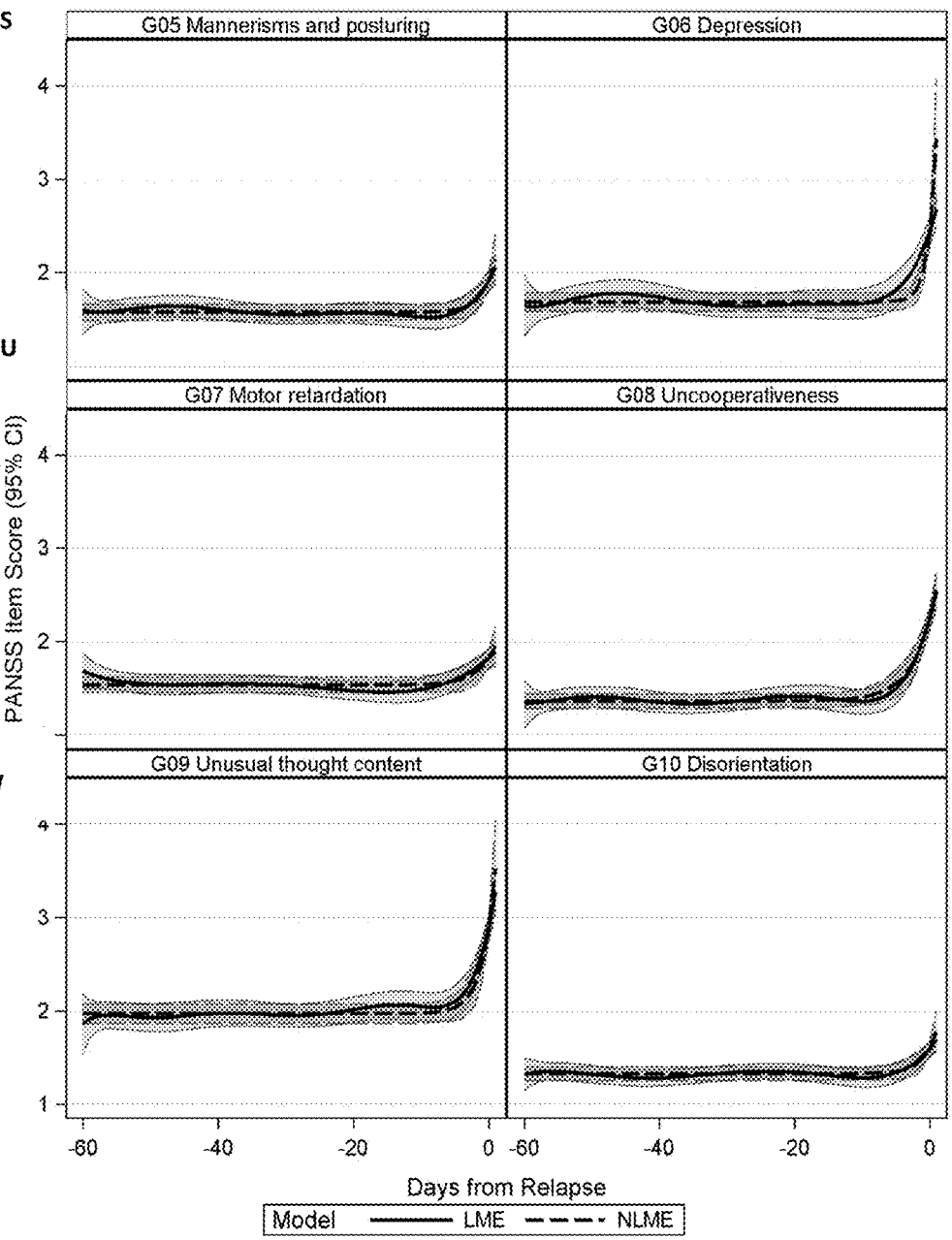

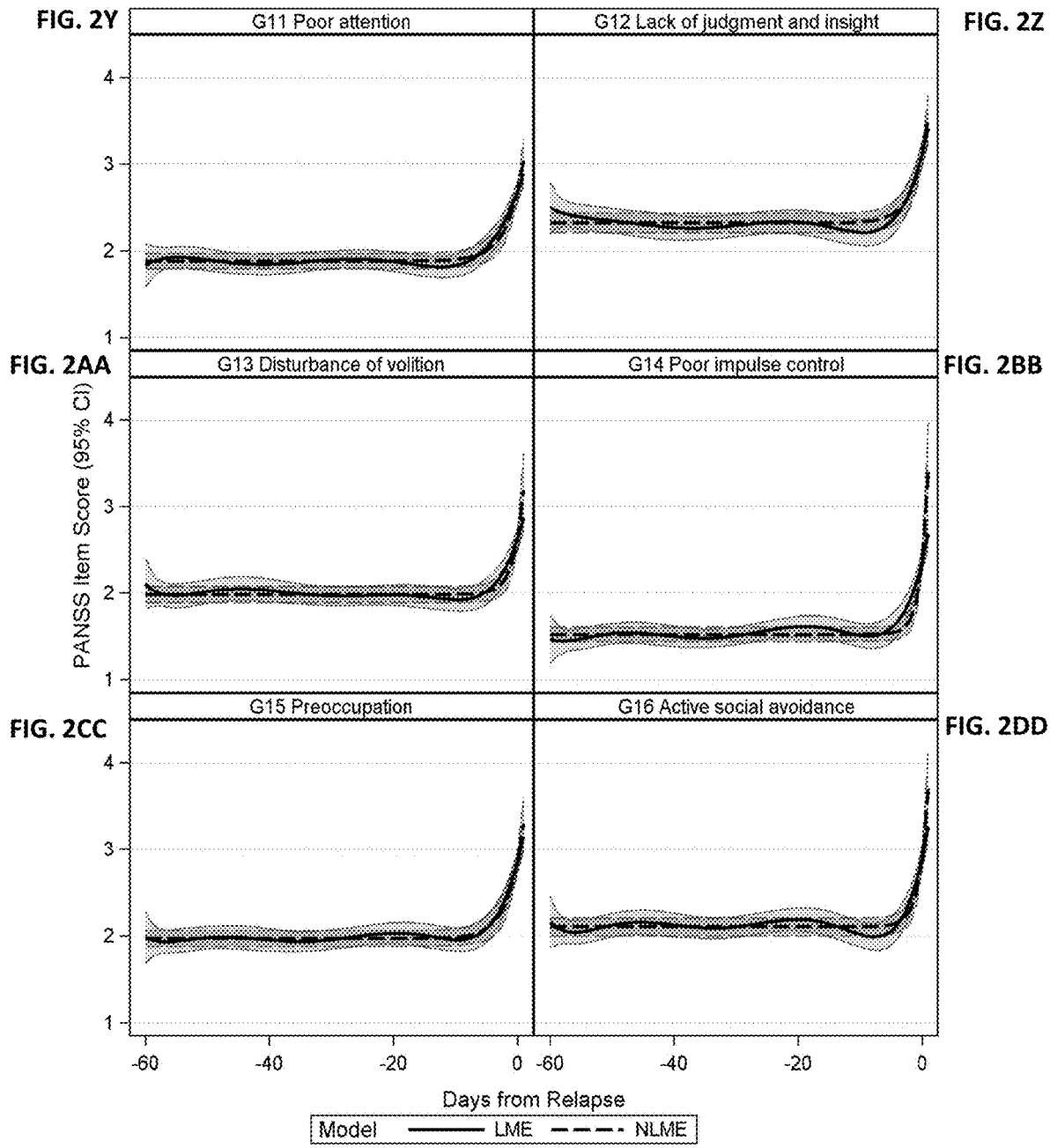

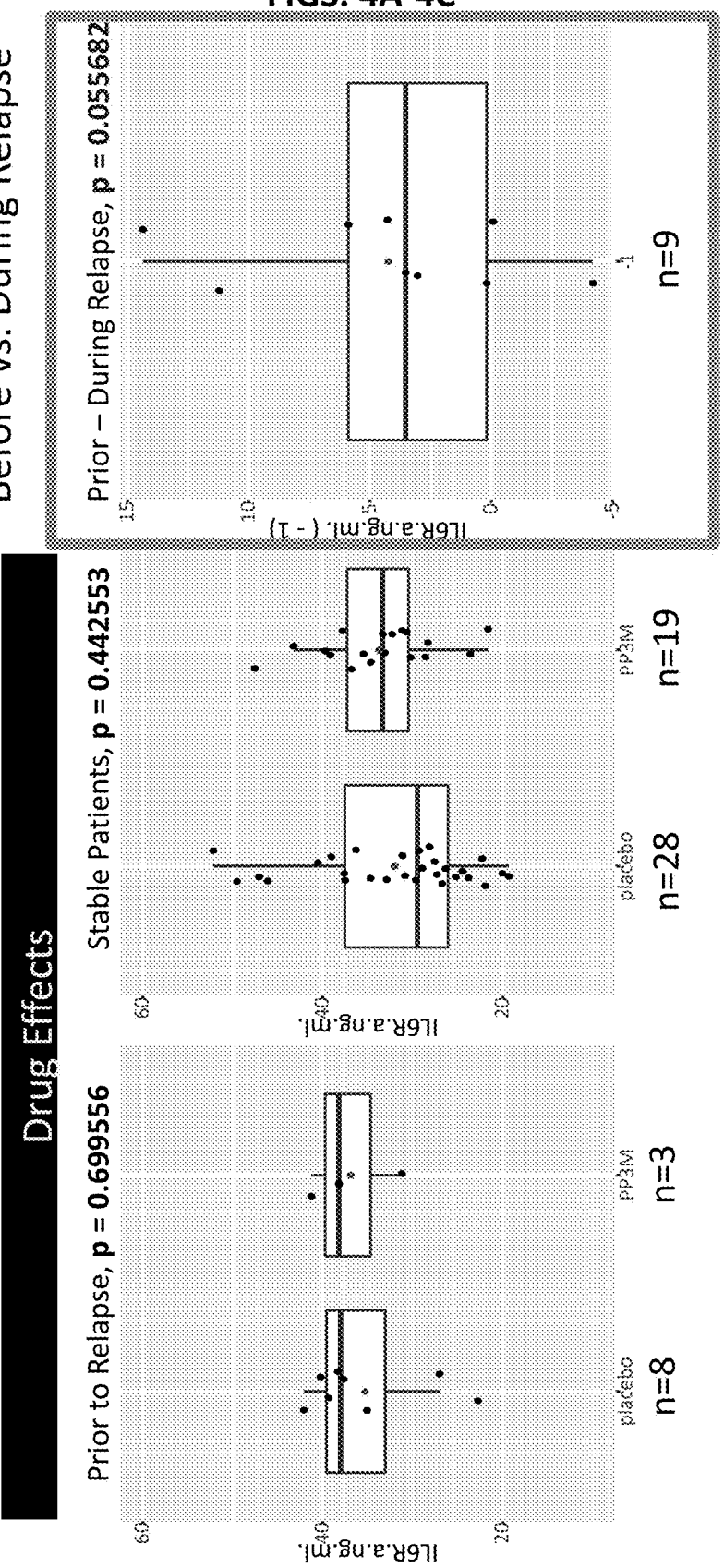

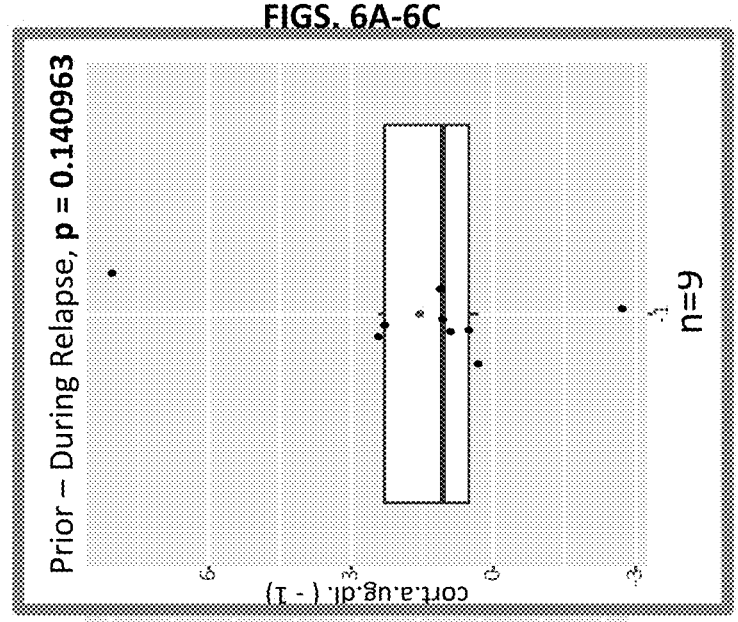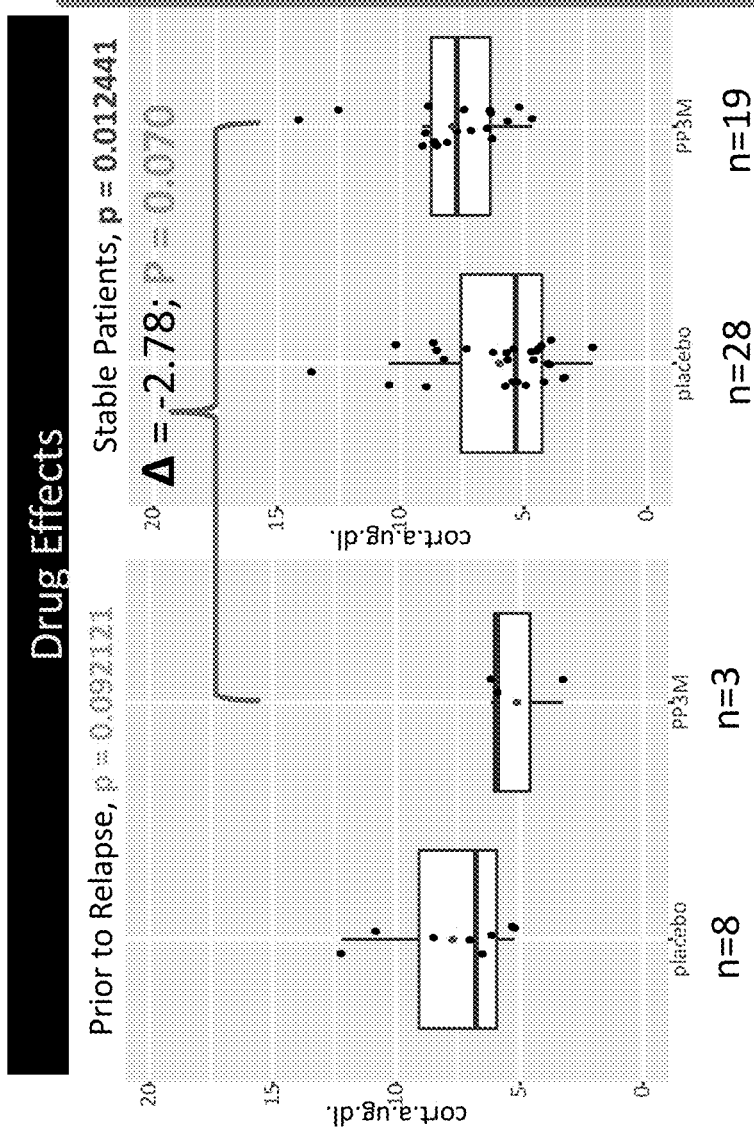
FIGS. 6A-6C

METHODS OF IDENTIFYING SCHIZOPHRENIA PATIENTS AT RISK FOR RELAPSE

PRIORITY CLAIM

This application claims priority to U.S. Provisional Application Ser. No. 62/434,587 filed on Dec. 15, 2016 and U.S. Provisional Application Ser. No. 62/425,257 filed on Nov. 22, 2016, the entireties of which are incorporated by reference herein their entirety.

FIELD OF THE INVENTION

This invention relates to methods of identifying patients at risk of a schizophrenic relapse in order to provide treatment to decrease the likelihood or severity of the relapse.

BACKGROUND

Schizophrenia is a complex, challenging, and heterogeneous psychiatric condition affecting an estimated 0.45%-1% of the world population (van Os & Kapur, 2009, Lancet 374:635-645). Patients suffering with schizophrenia present with a range of symptoms including positive symptoms, such as delusions, hallucinations, thought disorders, and agitation; negative symptoms, such as mood flatness and lack of pleasure in daily life; cognitive symptoms, such as the decreased ability to understand information and make decisions, difficulty focusing, and decreased working memory function; and sleep disorders.

Schizophrenia is a chronic disease that requires long-term treatment to achieve sustained symptom control, reduce the risk of relapse, improve patient functioning and overall quality of life (Andreasen, 1995, Lancet. 346(8973):477-81; Ascher-Svanum et al., 2006, J Clin Psychiatry 67(3):453-60; Keith et al. 2003, J Clin Psychiatry 64(11):1308-15). It is estimated that up to 75% of patients with schizophrenia have difficulty adhering to a daily oral treatment regimen of antipsychotics (Bhanji et al., 2004, 14(2):87-92). Poor adherence, particularly among persons early in the course of their illness, leads to worse long-term outcomes (including enhanced risk of relapse) than does consistent, well-documented treatment (Subotnik et al., 2011, Am J Psych 168(3): 286-292). Estimated one-year rates of nonadherence to medication regimen, such as treatment discontinuation or interruption, ranges from 40% to 75% (Bhanji et al., 2004, 14(2):87-92; Masand et al., 2009, 11(4):147-54; Weiden & Zygmunt, 1997, J Pract Psychiatr Behav Health 3:106-110). Although long-acting injectable (LAI) formulations of atypical antipsychotics have been developed in order to improve patient adherence, numerous challenges remain for adoption of these treatments into general psychiatric practice (Kane et al., 2014, J Clin Psychiatry 75(12): e33; Weiden et al., 2015, J Clin Psychiatry 76(6): 684-690). For example, it takes months for LAIs to achieve steady-state equilibrium, and knowing how to quickly transition patients from prior treatments to optimal doses of a new LAI regimen can be difficult.

Most schizophrenia patients experience multiple relapses during their disease course. Repeated relapses may lead to treatment resistance, cognitive impairment, decreased quality of life, and increased economic burden. Existing clinical practice is inefficient to detect relapse early. The symptoms of relapse usually develop in less than 4 weeks. Existing clinical practice typically have the patients come in for a check every month, which is inefficient to detect relapse early. Accordingly, there is an unmet need to detect patients that are at risk of relapse.

SUMMARY OF THE INVENTION

This invention relates to methods of identifying patients at risk of a schizophrenia relapse. The methods of the invention utilize a targeted set of interview-based observations and/or one or more biomarker levels to identify such patients.

In one embodiment, an increase in severity of newly identified subset of particular symptoms of schizophrenia indicate that a patient is at risk for schizophrenia relapse. In a specific embodiment, the particular symptoms are delusions, conceptual disorganization, hallucinations, excitement, suspiciousness, hostility, anxiety, tension and unusual thought content. In such an embodiment, at least 5, at least 6, at least 7, at least 8 or all 9 symptoms show an increase in severity as compared to one or more past assessments. In another specific embodiment, the particular symptoms are delusions, conceptual disorganization, hallucinations, excitement, anxiety, tension and unusual thought content. In such an embodiment, at least 4, at least 5, at least 6, or all 7 symptoms show an increase in severity as compared to one or more past assessments.

According to the invention, the symptoms can be assessed using any method. In a specific embodiment, the Positive and Negative Syndrome Scale (PANSS) is used and an increase in score in the particular items as compared to a previous score indicates a patient is at risk for schizophrenia relapse. In such an embodiment, methods of identifying a patient at risk for a schizophrenia relapse comprises scoring a patient on a subset of PANSS items and determining an amount of change in the score of the subset of PANSS items as compared to one or more previous PANSS items scores for the patient wherein an increase of at least 1 point in at least a majority of the scored PANSS items indicates the patient is at risk for a schizophrenic relapse.

In a specific embodiment, the PANSS items are P01 (delusions), P02 (conceptual disorganization), P03 (hallucinations), P04 (excitement), P06 (suspiciousness), P07 (hostility), G02 (anxiety), G04 (tension) and G09 (unusual thought content). In such an embodiment, at least 5, at least 6, at least 7, at least 8 or all 9 PANSS items show at least a 1 point increase as compared to one or more previous PANSS items scores.

In a more specific embodiment, the PANSS items are P01 (delusions), P02 (conceptual disorganization), P03 (hallucinations), P04 (excitement), P06 (suspiciousness), G02 (anxiety) and G04 (tension). In such an embodiment, at least 4, at least 5, at least 6, or all 7 PANSS items show at least a 1 point increase as compared to one or more previous PANSS items scores.

In another embodiment, an increased biomarker level in body fluid of a patient as compared to a previously measured biomarker level indicates a patient is at risk for schizophrenia relapse. Biomarkers are selected from the group consisting of interleukin 6 receptor (IL6R), interleukin 6 (IL6) and cortisol.

In such an embodiment, methods of identifying a patient at risk for a schizophrenia relapse comprises measuring the biomarker level in a body fluid of a patient, comparing the biomarker level in the body fluid of the patient to a previously measured biomarker level in the body fluid of the patient and determining the amount of change in the biomarker level. An increase in the biomarker level indicates the patient is at risk for a schizophrenic relapse.

In some embodiments, both the symptom subset severity (e.g., using PANSS scores) and biomarker levels are used to identify a patient at risk of a schizophrenic relapse.

Patients determined to be at risk of a schizophrenia relapse by the methods of the invention are administered a pharmaceutical agent or psychosocial intervention to decrease likelihood of progression to the relapse or the severity of the relapse. In some embodiments, the administered pharmaceutical agent is an atypical antipsychotic.

BRIEF DESCRIPTION OF THE DRAWINGS

FIGS. 1A-1D show the score of individual PANSS items at relapse. (A) relapse from randomization; (B) relapse defined by psychiatric event; (C) changes at relapse as compared to the last pre-relapse visit; (D) changes at relapse defined by psychiatric event as compared to the last pre-relapse visit.

FIGS. 4A-4C show the changes in IL6R from baseline in patients who relapsed. (A) Patients prior to relapse; (B) Stable patients; (C) comparison of biomarker change between prior to relapse and during relapse.

FIGS. 6A-6C show the changes in cortisol from baseline in patients who relapsed. (A) Patients prior to relapse; (B) Stable patients; (C) comparison of biomarker change between prior to relapse and during relapse.

DETAILED DESCRIPTION OF THE INVENTION

Figures 2A, 2B, 2C, 2D:
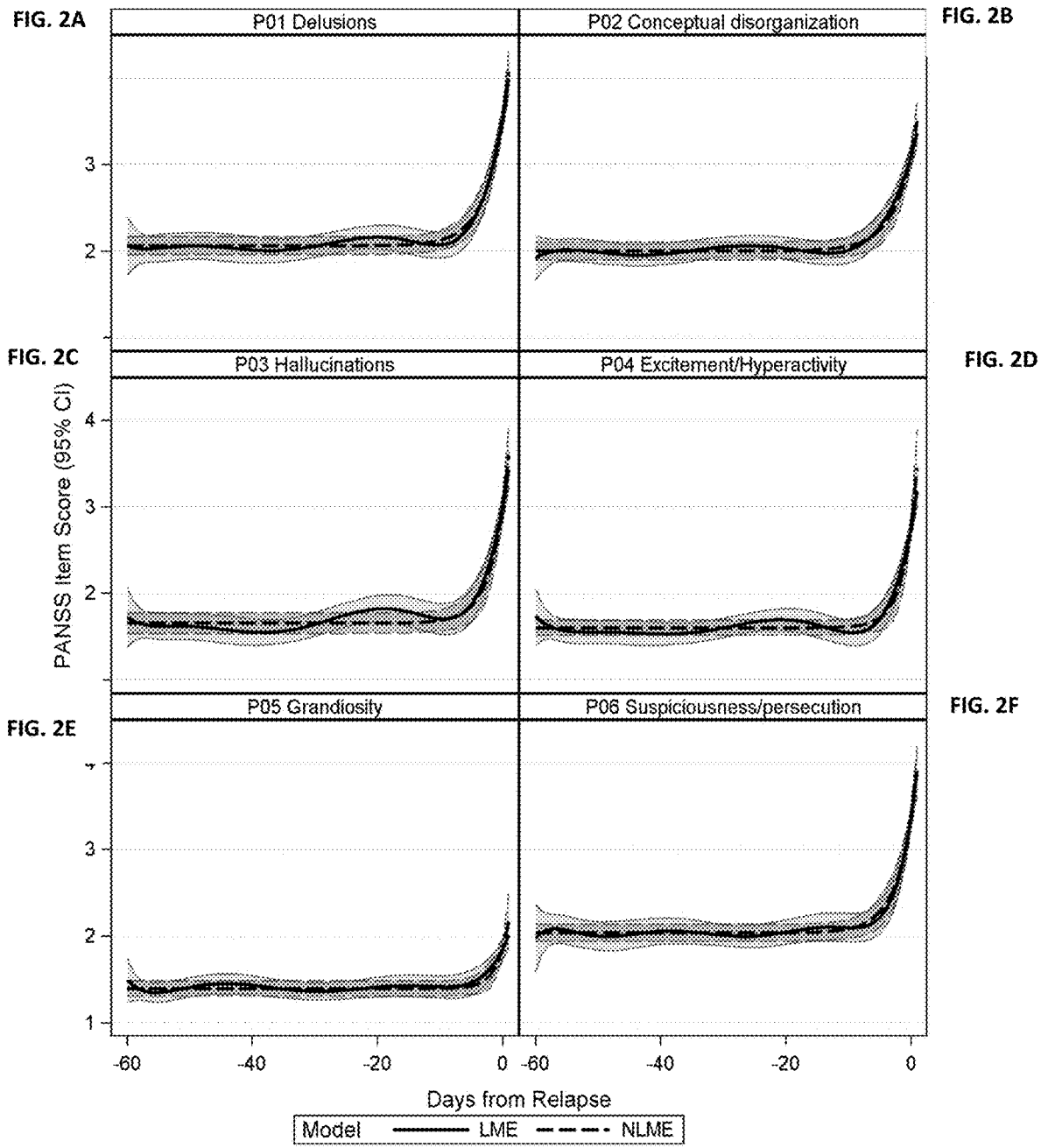
FIGS. 2A-2DD show trajectories of changes in all thirty individual PANSS items from their pre-relapse levels estimated from linear (LME) and non-linear (NLME) mixed effects models. (A) P1 delusions; (B) P2 conceptual disorganization; (C) P3 hallucinations; (D) P4 excitement; (E) P5 grandiosity; (F) P6 suspiciousness; (G) P7 hostility; (H) N1 blunted effect; (I) N2 emotional withdrawal; (J) N3 poor rapport; (K) N4 passive-apathetic social withdrawal; (L) N5 difficulty in abstract thinking; (M) N6 lack of spontaneity and flow of conversation; (N) N7 stereotyped thinking; (O) G1 somatic concern; (P) G2 anxiety; (Q) G3 guilt feelings; (R) G4 tension; (S) G5 mannerisms and posturing; (T) G6 depression; (U) G7 motor retardation; (V) G8 uncooperativeness; (W) G9 unusual thought content; (X) G10 disorientation; (Y) G11 poor attention; (Z) G12 lack of judgment and insight; (AA) G13 disturbance of volition; (BB) G14 poor impulse control; (CC) G15 preoccupation; (DD) G16 active social avoidance.

The present invention provides methods of identifying patients at risk of a schizophrenia relapse. In one embodiment, the patient monitored by the methods of the present invention has had only one episode of psychosis. In other embodiments, the patient monitored by the methods of the present invention has had more than one episode of psychosis. The methods of the invention can be used to monitor patients that are currently institutionalized (i.e., in a psychiatric facility) as well as those who are not (i.e., in a halfway house, living with a caregiver or living independently).

The inventors have identified a particular subset of symptoms that begin to increase in severity 7-10 days prior to a schizophrenia relapse. Symptom severity can be measured by any method known in the art. In one embodiment, symptom severity can be assessed using questions asked to the patient. The questions can be a self assessment by the patient, asked to the patient by a caregiver or asked to the patient by a healthcare provider.

In a particular embodiment, symptom severity can be measured using the PANSS assessment. The articular subset of PANSS items begin to increase in score 7-10 days prior to a relapse and reach an increase of at least 1 point 0.3-1.2 days before a relapse. The increased score is relative to one or more previous assessed PANSS item scores for the patient.

In one embodiment, methods of identifying a patient at risk for a schizophrenia relapse comprises scoring a patient on a subset of PANSS items and determining an amount of change in the score of the subset of PANSS items as compared to one or more previous PANSS items scores for the patient wherein an increase of at least 1 point in at least a majority of the scored PANSS items indicates the patient is at risk for a schizophrenic relapse.

In a specific embodiment, the PANSS items are P01 (delusions), P02 (conceptual disorganization), P03 (hallucinations), P04 (excitement), P06 (suspiciousness), P07 (hostility), G02 (anxiety), G04 (tension) and G09 (unusual thought content). In such an embodiment, at least 5, at least 6, at least 7, at least 8 or all 9 PANSS items show at least a 1 point increase as compared to one or more previous PANSS items scores.

In a more specific embodiment, the PANSS items are P01 (delusions), P02 (conceptual disorganization), P03 (hallucinations), P04 (excitement), P06 (suspiciousness), G02 (anxiety) and G04 (tension). In such an embodiment, at least 5, at least 5, at least 6, or all 7 PANSS items show at least a 1 point increase as compared to one or more previous PANSS items scores.

The inventors have also identified biomarkers that increase in level as compared to previously measured levels in the body fluid of a patient when a patient is at risk of a schizophrenic relapse. In some embodiments, the biomarkers are IL6R, IL6 and/or cortisol.

A combination of the PANSS scale and biomarker method of the invention can be used to identify patients at risk of a schizophrenic relapse.

Patients determined to be at risk of a schizophrenia relapse by the methods of the invention are administered a pharmaceutical agent to decrease likelihood of progression to the relapse or the severity of the relapse. In some embodiments, the administered pharmaceutical agent is an atypical antipsychotic.

PANSS

The positive and negative syndrome scale (PANSS) (Kay et al., 1987, Schizophr. Bull. 13:261-276) is a widely used medical scale for measuring symptom severity of patients with schizophrenia. The healthcare provider rates the patient as a 1 to 7 on 30 symptoms based on a clinical interview as well as reports of family members or primary care hospital workers. The 30 items are grouped into 3 subscales: positive scale (7 items), negative scale (7 items), and general psychopathology scale (16 items) (Table 1). The PANSS total score ranges from 30 to 210. The PANSS is typically administered when the patient is seen by a healthcare provider, at least every 4 weeks, preferably biweekly, more preferably every week. While these are the preferred intervals for evaluation, the patient may be administered the interview less frequently based on the patient's ability to attend appointments with the healthcare provider and/or the length of time it takes to administer the full PANSS assessment (about 1 hour).

The present invention has identified a subset of PANSS items that are predictive of a schizophrenic relapse and thus reduce the time of assessment by the healthcare provider as well as increase the predictive value of imminent relapse.

consecutive assessments for patients who scored >40 or a 10-point increase for patients who scored ≤40.

The methods of the present invention can be used to identify schizophrenic patients that are risk of relapse. One advantage of the present invention is that only a subset of PANSS items are used thus decreasing resource demands and the time it takes for patient evaluation. Additionally, the

TABLE 1

PANSS Items

| Positive Scale | Negative Scale | General Psychopathology Scale |
|---|---|---|
| P01 Delusions | N01 Blunted affect | G01 Somatic concern |
| P02 Conceptual disorganization | N02 Emotional withdrawal | G02 Anxiety |
| P03 Hallucinations | N03 Poor rapport | G03 Guilt feelings |
| P04 Excitement | N04 Passive-apathetic social withdrawal | G04 Tension |
| P05 Grandiosity | N05 Difficulty in abstract thinking | G05 Mannerisms & posturing |
| P06 Suspiciousness | N06 Lack of spontaneity & flow of conversation | G06 Depression |
| P07 Hostility | N07 Stereotyped thinking | G07 Motor retardation |
| | | G08 Uncooperativeness |
| | | G09 Unusual thought content |
| | | G10 Disorientation |
| | | G11 Poor attention |
| | | G12 Lack of judgment & insight |
| | | G13 Disturbance of volition |
| | | G14 Poor impulse control |
| | | G15 Preoccupation |
| | | G16 Active social avoidance |

Relapse

Relapse, characterized by acute psychotic exacerbation, may have serious implications. For example, there is a risk of patients harming themselves or others, of jeopardizing personal relationships, education or employment status (Kane, 2007, J Clin Psychiatry 68 (Suppl 14): 27-30), and of further stigmatization of the illness. Additionally, relapse may carry a biological risk. It has been proposed that active psychosis reflects a period of disease progression insofar as patients may not return to their previous level of function and treatment refractoriness may emerge (Wyatt, 1997, Schizophr Bull. 23: 3-9; Lieberman et al, 1996, Neuropsychopharmacol. 14: 13S-21S).

Reliable early warning signs of relapse offer the opportunity of early intervention and prevention of florid relapse. However, whereas the onset of a first episode of psychosis may be gradual and is typically heralded by a prodromal period lasting months to even years (Yung & McGorry et al., 1996, Schizophr Bull. 22: 353-370), this does not appear to be the case in relapse episodes. For these reasons it has been recommended that the term "prodromal symptoms" be restricted to precursors of a first psychotic episode and "early warning signs" be used to describe antecedents of psychotic relapse (Bustillo et al., 1995, Schizophr Bull. 21: 553-559). Prior to the present invention, studies suggested that it is difficult to identify many patients who are at risk of imminent relapse in clinical practice, and that early warning signs are relatively unreliable predictors of relapse (Norman & Malla, 1995, Schizophr Bull. 21: 527-539; Gaebel & Riesbeck, 2007, Schizophr Res. 95: 19-29, Gaebel et al, 1993, Br J Psychiatry Suppl. 21: 8-12).

Relapse can be defined by any one of the following criteria: 1) psychiatric hospitalization (involuntary or voluntary admission to a psychiatric hospital for decomposition of the patient's schizophrenia symptoms); 2) deliberate self-injury or aggressive behavior, or suicidal or homicidal ideation and aggressive behavior that was clinically significant; and 3) 25% increase in PANSS total score for two subset of PANSS items used allows the healthcare provider to focus on only those items relevant to prediction of relapse and thus decrease the noise of items less relevant to predication of relapse.

Remote Detection of Symptom Severity

In some embodiments of the present invention, the severity of the subset of symptoms (e.g. the PANSS item score) can be transmitted to a healthcare provider remotely thus increasing the number of assessments that can be taken due to the freedom from physically having to visit the healthcare provider. The patient or their caregiver can document the symptom severity (e.g., PANSS item score and/or other biometric data) without a healthcare provider present. Data can be conveniently entered onto the system while the user may continue to use the local computing device for other purposes. A local computing device may comprise, for example, a computing device worn on the body (e.g. a head-worn computing device such as a Google Glass, a wrist-worn computing device such as a Samsung Galaxy Gear Smart Watch, etc.), a tablet computer (e.g. an Apple iPad, an Apple iPod, a Google Nexus tablet, a Samsung Galaxy Tab, a Microsoft Surface, etc.), a smartphone (e.g. an Apple iPhone, a Google Nexus phone, a Samsung Galaxy phone, etc.).

In one embodiment, the data is collected and transmitted by an electronic device including, but not limited to, a wearable device that sends data to a healthcare provider. In another embodiment, an electronic questionnaire answered by the patient or their caregiver is used to transmit data to a healthcare provider. In another embodiment, a combination of an electronic device and an electronic questionnaire is used to transmit data to a healthcare provider.

In one embodiment, data concerning PANSS items P01, P02, P03, P04, P06, G02 and G04 are transmitted to the healthcare provider. A comparison can be made between the most recent transmitted data and data from one or more previous assessment. An increase in at least 4, at least 5, at least 6 or all 7 PANSS items alerts the healthcare provider that the patient is at risk for a schizophrenia relapse.

In another embodiment, data concerning PANSS items P01, P02, P03, P04, P06, P07, G02, G04 and G09 are transmitted to the healthcare provider. A comparison can be made between the most recent transmitted data and data from one or more previous assessments. An increase in at least 5, at least 6, at least 7, at least 8 or all 9 PANSS items alerts the healthcare provider that the patient is at risk for a schizophrenia relapse.

Biomarkers

A biomarker is a measurable indicator of a biological state or condition. The present invention identifies soluble biomarkers that show increased levels in body fluids of patients about to undergo or presently undergoing a schizophrenia relapse. Biomarker levels increase at least 1 month, at least 1 week, at least 3 days or at least 1 day prior to schizophrenia relapse.

According to the methods of the invention, biomarker level in a body fluid of a patient is measured and the amount of change in the biomarker level in the body fluid of the patient as compared to a previously measured biomarker level in the body fluid of the patient is determined. An increase in the biomarker level indicates the patient is at risk for a schizophrenic relapse. Patients have the biomarker level measured at least every month, at least every 2 weeks, at least every week.

In one embodiment, the biomarker is the interleukin 6 receptor (IL6R) or a fragment thereof. In a preferred embodiment, the IL6R is in soluble form. An increase of at least 4 ng/ml of IL6R in the body fluid of a patient as compared to a previously measured level in the patient indicates the patient is at risk for a schizophrenic relapse.

In another embodiment, the biomarker is interleukin 6 (IL6). An increase of at least 0.1 pg/ml of IL6 in the body fluid of a patient as compared to a previously measured level in the patient indicates the patient is at risk for a schizophrenic relapse.

In another embodiment, the biomarker is cortisol. An increase of at least 1 µg/ml of cortisol in the body fluid of a patient as compared to a previously measured level in the patient indicates the patient is at risk for a schizophrenic relapse.

One or more biomarkers can be used to identify a patient at risk of a schizophrenic relapse. In one embodiment, the level of one biomarker is detected in a patient. In another embodiment, two biomarker levels are detected in a patient. In yet another embodiment, three biomarker levels are detected in a patient.

Biomarkers can be detected in any body fluid including, but not limited to, blood, plasma, serum, lymph, saliva and urine. In preferred embodiments, the body fluid is blood.

Any method can be used to measure and quantify the biomarkers used in the methods of the invention. Methods to measure protein expression levels of biomarkers include, but are not limited to, western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), flow cytometry, and assays based on a property of the biomarker including but not limited to ligand binding, or interaction with other protein partners.

Pharmaceutical Agents

According to the methods of the present invention, a patient identified as at risk for schizophrenic relapse by scoring the subset of identified symptoms of interest and/or increase in biomarkers disclosed supra is administered a pharmaceutical agent to decrease likelihood of progression to the relapse or the severity of the relapse. The pharmaceutical agent can be administered to the patient by the healthcare provider on an in-patient or out-patient basis.

Pharmaceutical agents for use in the methods of the invention are any pharmaceutical agent useful for treating, ameliorating or preventing at least one symptom of schizophrenia. In a specific embodiment, the pharmaceutical agent is an atypical antipsychotic. In a more specific embodiment, the atypical antipsychotic is selected from the group consisting of risperidone, paliperidone, paliperidone palimatate, olanzapine, aripiprazole, quetiapine, ziprasidone, lurasidone, asenapine, cariprazine, brexpiprazole and clozapine. In a more specific embodiment, the atypical antipsychotic is risperidone, paliperidone, paliperidone palimitate.

EXAMPLES

The invention can be further understood in view of the following non-limiting examples.

Example 1

PANSS: Methods

Data were pooled from three randomized, double-blind (DB), placebo-controlled studies to determine the efficacy of paliperidone oral extended-release (ER) formulation, paliperidone palmitate 1-month injectable formulation (PP1M), and paliperidone palimtate 3-month injectable formulation (PP3M), respectively, in delaying psychosis relapse in adult patients with a diagnosis of schizophrenia by DSM-IV-TR criteria for at least one year. The 3 studies had similar study designs. Each study had a screen phase, an open-label run-in or transition phase during which eligible patients were transitioned to the study drug (or PP1M instead of PP3M for the PP3M study) and had their symptoms controlled, an open-label stabilization or maintenance phase during which stable patients received flexible doses of the study drug, and a double-blind phase during which stabilized patients were randomized in a 1:1 ratio to receive either study drug or placebo and were followed until they experienced a relapse, they withdrew from the study, or the study was completed. The differences in the study designs among the 3 studies were summarized in Table 2.

TABLE 2

| | Differneces in Study Designs | | |
|---|---|---|---|
| | Paliperidone ER NCT00086320 | PP1M NCT00111189 | PP3M NCT01529515 |
| Study Phases | 8 week run-in; 6 week stabilization; | 9 week transition; 24 week maintenance; | 17 week transition (treated with PP1M |

TABLE 2-continued

Differneces in Study Designs

| | Paliperidone ER NCT00086320 | PP1M NCT00111189 | PP3M NCT01529515 |
|---|---|---|---|
| | Double-blind relapse prevention | Double-blind relapse prevention | instead of PP3M); 12 week maintenance; Double-blind relapse prevention |
| Inclusion Criteria | PANSS total score in (70, 120) | PANSS total score <120 | PANSS total score <120 |
| Criteria to Enter Stabilization/ Maintenance | * PANSS total score <70 for at least 2 weeks<br>* A score of ≤4 for at least 2 weeks for PANSS items P1, P2, P3, P6, P7, G8<br>* CGI-S ≤4 for at least 2 weeks<br>* The dose of pali ER remains unchanged for at least 2 weeks | PANSS total score ≤75 at week 9 | PANSS total score ≤70 at week 17 |
| Criteria to Enter Double-blind Phase | * PANSS total score ≤70<br>* A score of ≤4 for each of the PANSS items P1, P2, P3, P6, P7, G8<br>* CGI-S ≤4<br>* The dose of pali ER remains unchanged | * PANSS total score ≤75<br>* A score of ≤4 for each of the PANSS items P1, P2, P3, P6, P7, G8, G14<br>* Stable dose of PP1M | * PANSS total score ≤70<br>* A score of ≤4 for each of the PANSS items P1, P2, P3, P6, P7, G8, G14 |

The detailed findings from these three studies were reported previously (Kramer et al., 2007, J. Clin. Psychopharmacol. 27:6-14; Hough et al., 2010, Schizophr. Res. 116:107-17; Berwaerts et al., 2015, JAMA Psychiatry 72:830-9). All the three formulations of paliperidone significantly delayed time-to-relapse of psychosis symptoms compared to placebo. All studies were conducted in accordance with the ethical principles in the Declaration of Helsinki, consistent Good Clinical Practices and applicable regulatory requirements. The study protocols and amendments were approved by an independent ethnic committee or an institutional review board for each site. All participants provided written informed consent.

The PANSS was administered every 4 weeks in these studies except in the paliperidone oral extended-release formulation study where it was administered weekly or biweekly into week 8 of the DB phase and every 4 weeks thereafter.

Example 2

PANSS: Definition of Relapse

The primary efficacy variable of these three studies was the time-to-first relapse during the DB phase. Relapse was defined by any one of the following criteria: 1) psychiatric hospitalization (involuntary or voluntary admission to a psychiatric hospital for decomposition of the patient's schizophrenia symptoms); 2) deliberate self-injury or aggressive behavior, or suicidal or homicidal ideation and aggressive behavior that was clinically significant; 3) 25% increase in PANSS total score for two consecutive assessments for patients who scored >40 at randomization, or a 10-point increase for patients who scored ≤40 at randomization; 4) increase for two consecutive assessments in pre-specified individual PANSS item scores (P1, P2, P3, P6, P7 and G8) to ≥5 for patients whose score was ≤3 at randomization, or to ≥6 for patients whose score was 4 at randomization. In the paliperidone ER study, relapse was also defined by a significant increase in the clinical global impression-severity (CGI-S) score. To make the relapse definition more homogenous across the three studies, this criterion was dropped for the paliperidone oral extended-release study. As a result, one patient's status was changed from relapse to non-relapse and was excluded from current analysis. There were 10 patients who did not meet the above criteria for relapse but were classified as patients who experienced a relapse. These 10 patients were also excluded from further analysis. There were also 14 patients who met the above criteria for relapse but were not called as relapse during the study. These 14 patients were reclassified as patients who experienced a relapse.

Example 3

PANSS: Statistical Analysis

Individual PANSS items were sorted by their changes at relapse from randomization as well as from the last pre-relapse visit in patients who experienced a relapse to see which PANSS items had the most increases at relapse. As the most common relapse reasons for this dataset were PANSS total and/or item score increase, individual PANSS items were also sorted by their changes at relapse in patients with relapse reasons other than PANSS total and/or item scores increase to see whether the same set of PANSS items had the most increase.

Linear and non-linear mixed effect models were applied to model the trajectories of individual PANSS items from a stable state to the time of relapse in patients who experienced a relapse during the double-blind phase of the three studies. PANSS item scores at the time of relapse, at the last pre-relapse visit, and during up to 8 weeks before the last pre-relapse visit were included in the analysis. For the paliperidone ER study, up to 7 PANSS assessments of each patient were included in the analysis. For the remaining two studies, up to 4 PANSS assessments of each patient were included in the analysis. The earliest PANSS assessment included in the analysis was at week 6 of the run-in phase for the ER study, at week 8 of the maintenance phase for the PP1M study, and at week 17 of the transition phase of the P3MM study. Patients who entered the double-blinded phase later already reached stable state at these visits.

Let $Y_{ij}$ the jth observation of a PANSS item on the ith patient and $T_{ij}$ be the days from relapse for the observation with i=1, n and j=1, ..., $n_i$. In the linear mixed effect model, the trajectory of an individual PANSS item was modeled as $$Y_{ij} \sim \text{polynomial}(T_{ij}) + \beta_{0,i} + \beta_{1,i} * T_{ij} + \varepsilon_{ij},$$

where polynomial($T_{ij}$) was a polynomial function of $T_{ij}$ with an order up to 7, $\beta_{0,i} \sim N(0, \sigma_0^2)$ and $\beta_{1,i} \sim N(0, \sigma_1^2)$ were subject-level intercept and slope for modeling the correlations among repeated measures, and $\varepsilon_{ij}$ was the observational error. The order of the polynomial function was determined through model selection using the Akaike information criteria.

In the non-linear mixed effect model, the trajectory of an individual PANSS item was modeled as an exponential function:

$$Y_{ij} \sim a^{(T_{ij}-b)} + c + \delta_i + \varepsilon_{ij},$$

where $\delta_i \sim N(0, \sigma_\delta^2)$ was a subject-level random effect included in the model to account for the correlations among repeated measures and $\Sigma_{ij}$ was the observational error. Compared to the polynomial function used in the linear mixed effect model, the exponential function used in the non-linear mixed effect model made stronger assumption regarding the shape of the trajectory, i.e., the individual PANSS items score increased exponentially before relapse. However, the parameters of the exponential function could be easily interpreted. The parameter a was an indicator of the speed of PANSS item increase before relapse. A smaller a parameter indicated the PANSS item increased relatively slowly before relapse thus may start to increase early. The parameter b represented the number of days before relapse when the PANSS item has 1-point of increase from its pre-relapse level. A negative b parameter indicates the patients will have on average more than 1-point increase on the PANSS item before relapse. The parameter c was the average pre-relapse level of the PANSS item.

Example 4

PANSS: Demographics and Characteristics of Patients Experienced a Relapse During Double-Blind Phase A total of 267 patients experienced a relapse during the double-blind phase of the three studies. Among these relapsed patients, 80, 126, and 61 patients were from the oral ER formulation study, the PP1M formulation study, and the PP3M formulation study, respectively. Within each study, there was no significant difference in age, gender, race, age at schizophrenia diagnosis, and baseline body mass index between patients who experienced a relapse and patients who discontinued from or completed the study without a relapse. An exception was in the PP1M study where patients who experienced a relapse had higher PANSS total score at the baseline of the DB phase (Table 3-5).

TABLE 3

Oral ER formulation study (R076477SCH-301)

| | Relapse | Non-relapse | p-value |
|---|---|---|---|
| N | 80 | 124 | |
| Age, years, Mean (SD) | 37.7 (10.2) | 38.5 (10.8) | 0.66 |
| Male, N (%) | 44 (55) | 77 (62.1) | 0.31 |
| Race, N (%) | | | |
| White | 60 (75) | 63 (50.8) | 0.0017 |
| Black | 7 (8.8) | 9 (7.3) | |
| Asian | 1 (1.3) | 2 (1.6) | |
| Other | 12 (15) | 50 (40.3) | |
| Age at schizophrenia diagnosis, Years, Mean (SD) | 26.1 (9.3) | 26.6 (9.2) | 0.67 |
| Body Mass Index, kg/m2, Mean (SD) | 27.4 (7.5) | 25.1 (6.1) | 0.02 |
| PANSS total score at DB phase baseline, Mean (SD) | 53.8 (10.6) | 51.1 (11.2) | 0.07 |
| Treatment | | | |
| Paliperidone ER | 26 (32.5) | 78 (62.9) | |
| Placebo | 54 (67.5) | 46 (37.1) | | p-values in red should not be interpreted due to the confounding effect from race.

TABLE 4

PP1M formulation study (R092670-PSY-3001)

| | Relapse | Non-relapse | p-value |
|---|---|---|---|
| N | 126 | 273 | |
| Age, Years, Mean (SD) | 39.3 (10.9) | 39 (11.1) | 0.75 |
| Male, N (%) | 67 (53.2) | 147 (53.8) | 0.9 |
| Race | | | |
| White | 81 (64.3) | 184 (67.4) | 0.09 |
| Black | 20 (15.9) | 54 (19.8) | |
| Asian | 24 (19) | 29 (10.6) | |
| Other | 1 (0.8) | 6 (2.2) | |
| Age at schizophrenia diagnosis, Years, Mean (SD) | 27.6 (9) | 27 (9.2) | 0.52 |
| Body Mass Index, kg/m2, Mean (SD) | 27.3 (6.2) | 27.2 (5.7) | 0.89 |
| PANSS total score at DB phase baseline, Mean (SD) | 55.2 (11.7) | 51.6 (11.8) | 0.005 |
| Treatment | | | |
| PP1M | 32 (25.4) | 168 (61.5) | |
| Placebo | 94 (74.6) | 105 (38.5) | |

TABLE 5

PP3M formulation study (R092670PSY3012)

| | Relapse | Non-relapse | p-value |
|---|---|---|---|
| N | 61 | 243 | |
| Age, Years, Mean (SD) | 37.3 (11.2) | 37.8 (11) | 0.73 |
| Male, N (%) | 47 (77) | 180 (74.1) | 0.63 |
| Race | | | |
| White | 37 (60.7) | 157 (64.6) | 0.21 |
| Black | 14 (23) | 31 (12.8) | |
| Asian | 4 (6.6) | 25 (10.3) | |
| Other | 6 (9.8) | 30 (12.3) | |
| Age at schizophrenia diagnosis, Years, Mean (SD) | 26.2 (8.9) | 27.1 (8.6) | 0.41 |
| Body Mass Index, kg/m2, Mean (SD) | 26.5 (4.4) | 26.1 (4.6) | 0.48 |
| PANSS total score at DB phase baseline, Mean (SD) | 56 (8.2) | 54.2 (10) | 0.3 |

TABLE 5-continued

PP3M formulation study (R092670PSY3012)

| Treatment | Relapse | Non-relapse | p-value |
|---|---|---|---|
| PP3M | 14 (23) | 146 (60.1) | |
| Placebo | 47 (77) | 97 (39.9) | |

Example 5

PANSS Items with Most Increases at Relapse

Among the 267 relapsed patients, a subset of 7 PANSS items had on average more than 1-point of increase at relapse from randomization (FIG. 1A). These 7 PANSS items included P1 [delusions] (mean change (standard error): 1.53 (0.08)), P2 [conceptual disorganization] (1.12 (0.07)), P3 [hallucinations] (1.44 (0.09)), P4 [excitement] (1.29 (0.07)), and P6 [suspiciousness] (1.49 (0.08)) from the positive symptom subscale as well as G2 [anxiety] (1.32 (0.07)) and G4 [tension] (1.24 (0.07)) from the general psychopathology subscale. Similar patterns were observed among patients whose relapses were defined by psychiatric events (FIG. 1B) as well as for changes at relapse from the last pre-relapse visit (FIG. 1C) and for changes at relapse defined by psychiatric events from the last pre-relapse visit (FIG. 1D).

Example 6

Trajectories of PANSS Items Increase Before Relapse

Figure 3:
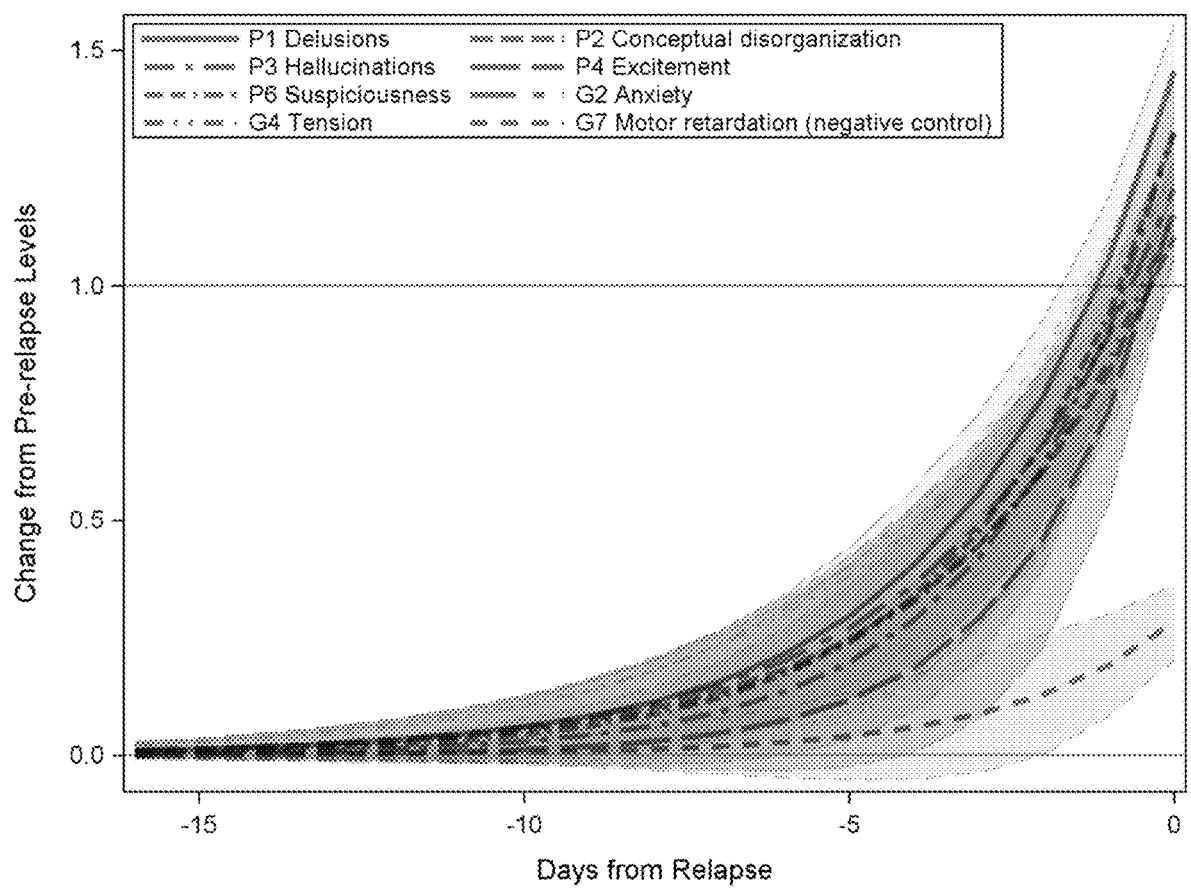
FIG. 3 shows trajectories of changes in eight individual PANSS items from their pre-relapse levels estimated from non-linear mixed effects models.
Figures 5A, 5B, 5C:
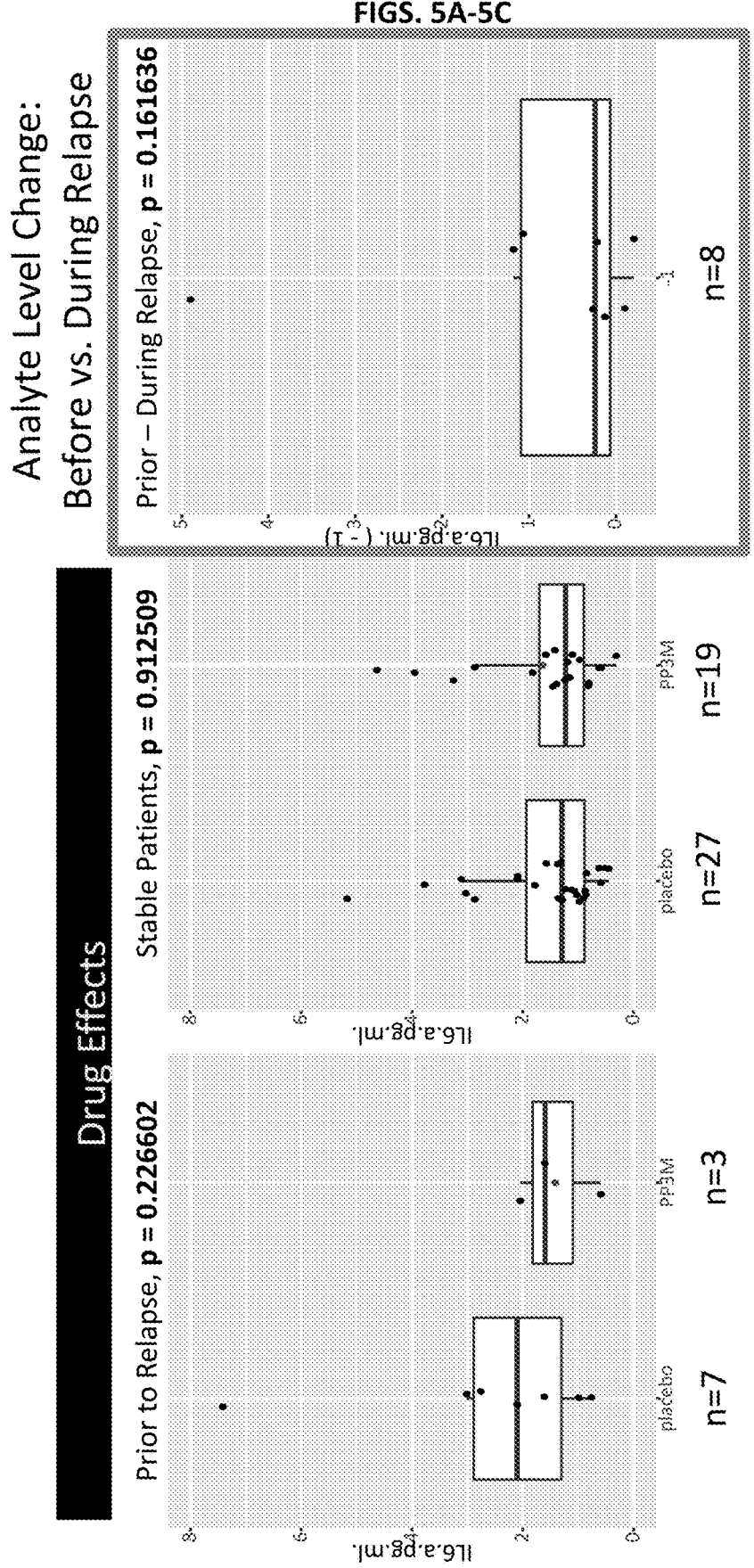
FIGS. 5A-5C show the changes in IL6 from baseline in patients who relapsed. (A) Patients prior to relapse; (B) Stable patients; (C) comparison of biomarker change between prior to relapse and during relapse.

The trajectories of individual PANSS items before relapse estimated from the linear and non-linear mixed effect models were similar (FIGS. 2A-2DD). The trajectories estimated from the non-linear mixed effect models were focused on because the parameters of these models can be easily interpreted. FIG. 3 shows the trajectories and their 95% confidence intervals of the 7 individual PANSS items that changed most at relapse as well as a negative control (an individual PANSS item with little increase (G7 [Motor retardation]) at relapse). The trajectories of the PANSS items that changed most at relapse suggested that these items started to increase about 7-10 days before relapse.

Table 6 shows the PANSS items with the most increases at relapse.

TABLE 6

PANSS items with most increases at relapse

| | From Randomization to Relapse | | From Last Pre-relapse Visit to Relapse | |
|---|---|---|---|---|
| Rank | Relapsed Patients | Patients with Relapse Reasons Other Than PANSS Total/Item Score Increase | Relapsed Patients | Patients with Relapse Reasons Other Than PANSS Total/Item Score Increase |
| 1 | P01 | P03 | P01 | P01 |
| 2 | P06 | P01 | P06 | P03 |
| 3 | P03 | P04 | P03 | P04 |
| 4 | G02 | G02 | G02 | P07 |
| 5 | P04 | P07 | G04 | G04 |
| 6 | G04 | P06 | P04 | P06 |
| 7 | P02 | G04 | P02 | G02 |
| 8 | G09 | G09 | P07 | G14 |
| 9 | P07 | P02 | G09 | P02 |
| 10 | G15 | G14 | G15 | G09 |

P01: Delusions; P02: Conceptual disorganization; P03: Hallucinations; P04: Hyperactivity/Excitement; P06: Suspiciousness/Persecution; P07: Hostility; G02: Anxiety; G04 Tension; G09: Unusual thought content; G14: Poor impulse control; G15: Preoccupation.

The b parameter in the non-linear mixed effect models represented the number of days before relapse when the individual PANSS item had 1-point of increase from its pre-relapse level. The b parameter estimates of the 7 PANSS items that changed most at relapse were less than 0 (Table 7), indicating these PANSS items would have on average more than 1-point of increase before relapse. The number of days before relapse when the individual PANSS item had on-average 1-point of increase from its pre-relapse level was 1.17 for P1 [Delusions], 0.84 for P6 [Suspiciousness], 0.74 for P3 [Hallucinations], 0.63 for G2 [Anxiety], 0.44 for G4 [Tension], 0.33 for P4 [Excitement], and 0.33 for P2 [Conceptual disorganization].

TABLE 7

The b parameter estimated from non-linear mixed effect models

| Rank | PANSS Item | Estimate | Std Err |
|---|---|---|---|
| 1 | P01 Delusions | −1.17 | 0.22 |
| 2 | P06 Suspiciousness | −0.82 | 0.21 |
| 3 | P03 Hallucinations | −0.74 | 0.21 |
| 4 | G02 Anxiety | −0.63 | 0.19 |
| 5 | G04 Tension | −0.44 | 0.16 |
| 6 | P04 Excitement | −0.33 | 0.14 |
| 7 | P02 Conceptual disorganization | −0.33 | 0.16 |
| 8 | P07 Hostility | 0.09 | 0.05 |
| 9 | G09 Unusual thought content | 0.16 | 0.09 |
| 10 | G14 Poor impulse control | 0.22 | 0.07 |
| 11 | G15 Preoccupation | 0.31 | 0.13 |
| 12 | G16 Active social avoidance | 0.34 | 0.09 |
| 13 | G06 Depression | 0.36 | 0.09 |
| 14 | G08 Uncooperativeness | 0.43 | 0.19 |
| 15 | G12 Lack of judgment & insight | 0.56 | 0.17 |
| 16 | N07 Stereotyped thinking | 0.58 | 0.18 |
| 17 | G11 Poor attention | 0.62 | 0.19 |
| 18 | G13 Disturbance of volition | 0.71 | 0.20 |
| 19 | N06 Lack of spontaneity & flow of conversation | 0.82 | 0.29 |
| 20 | N03 Poor rapport | 0.84 | 0.23 |
| 21 | N01 Blunted affect | 1.11 | 0.33 |
| 22 | N02 Emotional withdrawal | 1.14 | 0.36 |
| 23 | G01 Somatic concern | 1.19 | 0.40 |
| 24 | N04 Passive-apathetic social withdrawal | 1.23 | 0.41 |
| 25 | P05 Grandiosity | 1.48 | 0.55 |
| 26 | G03 Guilt feelings | 1.61 | 0.57 |
| 27 | N05 Difficulty in abstract thinking | 1.66 | 0.62 |
| 28 | G05 Mannerisms & posturing | 2.10 | 0.91 |
| 29 | G10 Disorientation | 2.58 | 1.15 |
| 30 | G07 Motor retardation | 3.23 | 1.91 |

Example 7

PANSS: Discussion

Consistent with previous observation, relapse is abrupt in schizophrenia patients. The individual PANSS items started to increase about 7-10 days before relapse and reached on average 1-point of increase as compared to previous PANSS scoring about 0.3-1.2 days before relapse. Thus, close monitoring is needed for early detection of relapse.

A subset of PANSS items (P1, P2, P3, P4, P6, G2, and G4) had more increases than other items immediately before relapse. These individual PANSS items included P1 [delusions], P2 [conceptual disorganization], P3 [Hallucinations], P4 [excitement], P6 [suspiciousness] from the Positive Symptoms Subscale and G2 [anxiety] and G4 [tension] from the General Psychopathology Subscale. Focusing on this subset of items offer the opportunity to intervene prior to an actual relapse event.

Example 8

Biomarker: Methods

Biomarkers of schizophrenia relapse were examined in a randomized, double-blind (DB), placebo-controlled study. The study was done to evaluate the efficacy and safety of the 3-month formulation of paliperidone palmitate (PP3M) vs placebo in delaying time to relapse of schizophrenia symptoms in patients previously treated with once-monthly paliperidone palmitate (PP1M) for at least 4 months (Beernaert's et al., 2015, JAMA Psychiatry 72(8):830-839). Biomarker collection was added as an amendment after the study had been partially completed. Sixty three patients had biomarker data collected. The study was conducted in accordance with the ethical principles in the Declaration of Helsinki, consistent Good Clinical Practices and applicable regulatory requirements.

Patients received PP1M (50, 75, 100, or 150 mg eq.) during 17-week transition phase, followed by PP3M (3.5× stabilized dose of PP1M) during 12-week maintenance phase. Stabilized patients were randomized (1:1) to fixed dose of PP3M (175, 263, 350, or 525 mg eq.) or placebo during the DB phase. Patient blood was sampled from week 17 and every 4 weeks thereafter until study end for biomarker evaluations. Patient blood was analyzed for the following biomarkers: leptin, adiponectin, mature BDNF, IGF1, cortisol, CRP, TNFα, IL1-β, IL6, IL6 receptor (IL6R), IL10, gp130 and interleukin-1 receptor antagonist (IL1RA). Analyte levels were measured using ELISA.

Example 9

Biomarker: Results

Forty seven patients were stable before the study end (n=19 PP3M vs. n=28 placebo). Sixteen patients relapsed during the study. Fourteen of the relapsed patients had biomarker measurement performed before relapse. Nine of the relapsed patients with biomarker measurements had measurements prior to and during the relapse point. Interleukin 6 receptor (IL6R) showed statistically significant changes from prior-to-relapse to relapse (p=0.05) (see FIGS. 4A-4C). Cortisol showed the largest difference between PP3M-treated stable patients and those prior to relapse (see FIGS. 6A-6C). Table 8 shows the change in biomarker levels in patients during relapse as compared to biomarker level prior to relapse. For all biomarkers, 1 or 2 patients showed large changes from prior-to-relapse to relapse, suggesting possibility of relapse processes that are accompanied by hormonal, metabolic or inflammatory changes.

TABLE 8

Change in Analyte Levels in Patients Before and During Relapse

| Bio-marker | \multicolumn{9}{c}{Patients} |
|---|---|---|---|---|---|---|---|---|---|
| | 1* | 2 | 3 | 4 | 5* | 6 | 7 | 8 | 9 |
| Cortisol | 0.32 | 0.52 | 8.04 | 2.30 | 1.07 | 0.91 | −2.72 | 1.12 | 2.43 |
| Leptin | 3.44 | 7.55 | −0.07 | 5.05 | 0.68 | 143.57 | 9.93 | −0.65 | 0.99 |
| Adiponectin | 1935.59 | −1986.66 | −13445.12 | 1835.28 | −492.55 | −10367.12 | −169.01 | 9419.08 | −2389.21 |
| Mature BDNF | −18524.28 | −1413.76 | −6203.35 | 15544.05 | −11787.39 | 11110.55 | −87.11 | −8437.21 | −9600.97 |
| CRP | −8.00 | 0.30 | 1.61 | 0.93 | 0.41 | 3.41 | 1.81 | 8.11 | 1.99 |
| IL6R | −4.18 | 0.21 | −0.06 | 3.55 | 14.38 | 3.06 | 4.30 | 5.91 | 11.24 |
| IGF1 | 18.30 | 11.10 | 16.25 | −42.95 | −11.45 | 81.35 | −0.25 | −7.50 | 18.75 |
| IL1RA | −74.26 | 138.42 | 505.39 | 102.79 | 114.31 | 464.67 | −626.22 | −965.22 | 51.29 |
| Gp130 | 46.60 | −45.60 | −17.70 | 17.80 | 9.20 | 10.10 | −76.60 | 35.70 | 17.70 |
| TNFα | −1.41 | NA | 3.44 | 1.24 | −0.95 | −0.56 | 0.16 | −0.24 | 3.68 |
| IL6 | 0.22 | NA | 1.18 | 0.26 | 0.13 | 1.07 | −0.21 | 4.90 | −0.10 |
| IL10 | 0.14 | 0.10 | 7.65 | 0.00 | 0.35 | 0.35 | 0.01 | 0.19 | 0.98 |
| IL1β | −0.03 | NA | −0.01 | 0.08 | 0.05 | −0.01 | 0.86 | −1.10 | NA |

*Patients received PP3M. All others were on placebo.
Bolded and underlined numbers represent values that are greater than 1 standard deviation away from the mean difference across samples.

What is claimed is:

1. A method of treating a patient at risk for a schizophrenia relapse comprising:
   a) scoring a patient on the following 7 Positive and Negative Syndrome Scale (PANSS) items before the schizophrenia relapse:
      P1 (delusions),
      P2 (conceptual disorganization),
      P3 (hallucinations),
      P4 (excitement),
      P6 (suspiciousness),
      G2 (anxiety), and
      G4 (tension);
   b) determining an amount of change in the score of the 7 PANSS items as compared to a previous PANSS score for the patient, wherein an increase of at least 1 point in all 7 of the 7 PANSS items identifies the patient as at risk for the schizophrenia relapse; and c) administering a pharmaceutical agent to the patient who has been found to be at risk in step (b) to decrease likelihood of progression to the relapse or severity of the relapse.

2. The method of claim 1, wherein the pharmaceutical agent is an atypical antipsychotic.

3. The method of claim 2, wherein the atypical antipsychotic is selected from the group consisting of: risperidone, paliperidone, paliperidone palmitate, olanzapine, aripiprazole, quetiapine, ziprasidone, lurasidone, asenapine, cariprazine, brexpiprazole and clozapine.

4. The method of claim 2, wherein the atypical antipsychotic is paliperidone or paliperidone palmitate.

5. The method of claim 1, wherein the scoring of the patient is conducted at least in part remotely.

6. The method of claim 5, wherein the scoring of a patient remotely is conducted at least in part by a wearable device that sends data to a healthcare provider or an electronic questionnaire answered by the patient or a caregiver of the patient.

7. The method of claim 4, wherein the atypical antipsychotic is paliperidone palmitate.

8. A method of treating a patient at risk for a schizophrenia relapse comprising:

a) scoring a patient on the following 9 Positive and Negative Syndrome Scale (PANSS) items before the schizophrenia relapse:
P1 (delusions),
P2 (conceptual disorganization),
P3 (hallucinations),
P4 (excitement),
P6 (suspiciousness),
P7 (hostility),
G2 (anxiety),
G4 (tension), and
G9 (unusual thought content);

b) determining an amount of change in the score of the 9 PANSS items as compared to a previous PANSS score for the patient, wherein an increase of at least 1 point in at least 7 of the 9 PANSS items identifies the patient as at risk for the schizophrenia relapse; and c) administering a pharmaceutical agent to the patient who has been found to be at risk in step (b) to decrease likelihood of progression to the relapse or severity of the relapse.

9. The method of claim 8, wherein an increase of at least 1 point in at least 8 of the 9 PANSS items identifies the patient as at risk for a schizophrenia relapse.

10. The method of claim 8, wherein an increase of at least 1 point in all 9 of the 9 PANSS items identifies the patient as at risk for a schizophrenia relapse.

11. The method of claim 8, wherein the pharmaceutical agent is an atypical antipsychotic.

12. The method of claim 11, wherein the atypical antipsychotic is selected from the group consisting of: risperidone, paliperidone, paliperidone palmitate, olanzapine, aripiprazole, quetiapine, ziprasidone, lurasidone, asenapine, cariprazine, brexpiprazole and clozapine.

13. The method of claim 12, wherein the atypical antipsychotic is paliperidone or paliperidone palmitate.

14. The method of claim 8, wherein the scoring of the patient is conducted at least in part remotely.

15. The method of claim 14, wherein the scoring of a patient remotely is conducted at least in part by a wearable device that sends data to a healthcare provider or an electronic questionnaire answered by the patient or a caregiver of the patient.

16. The method of claim 13, wherein the atypical antipsychotic is paliperidone palmitate.

17. A method of treating a patient at risk for a schizophrenia relapse comprising:

a) determining the severity of the following symptoms in a patient before the schizophrenia relapse:
delusions,
conceptual disorganization,
hallucinations,
excitement,
suspiciousness,
anxiety, and
tension; and b) determining an amount of change in the severity of the symptoms as compared to a previous assessment for the patient, wherein an increase in symptom severity in all 7 of the 7 symptoms identifies the patient as at risk for the schizophrenia relapse, and c) administering a pharmaceutical agent to the patient who has been found to be at risk in step (b) to decrease likelihood of progression to the relapse or severity of the relapse.

18. The method of claim 17, wherein the atypical antipsychotic is selected from the group consisting of: risperidone, paliperidone, paliperidone palmitate, olanzapine, aripiprazole, quetiapine, ziprasidone, lurasidone, asenapine, cariprazine, brexpiprazole and clozapine.

19. The method of claim 18, wherein the atypical antipsychotic is paliperidone or paliperidone palmitate.

20. The method of claim 19, wherein the atypical antipsychotic is paliperidone palmitate.

\* \* \* \* \*